i
US009993354B2

(12) United States Patent
Fisher et al.

(10) Patent No.: US 9,993,354 B2
(45) Date of Patent: *Jun. 12, 2018

(54) SENSING FORCE DURING PARTIAL AND TOTAL KNEE REPLACEMENT SURGERY

(75) Inventors: Michael G. Fisher, Folsom, CA (US);
Andrew Sizelove, Folsom, CA (US);
Keith R. Berend, New Albany, OH (US); David Murray, Oxford (GB)

(73) Assignee: Synvasive Technology, Inc., El Dorado Hills, CA (US)

( * ) Notice: Subject to any disclaimer, the term of this patent is extended or adjusted under 35 U.S.C. 154(b) by 1131 days.

This patent is subject to a terminal disclaimer.

(21) Appl. No.: 13/472,785

(22) Filed: May 16, 2012

(65) Prior Publication Data

US 2012/0232429 A1 Sep. 13, 2012

Related U.S. Application Data

(62) Division of application No. 12/544,897, filed on Aug. 20, 2009, now Pat. No. 8,211,041.

(Continued)

(51) Int. Cl.
*A61F 2/46* (2006.01)
*A61F 2/38* (2006.01)
(Continued)

(52) U.S. Cl.
CPC ............ *A61F 2/4657* (2013.01); *A61B 17/88* (2013.01); *A61F 2/38* (2013.01); *A61F 2/32* (2013.01);
(Continued)

(58) Field of Classification Search
CPC .. A61F 2/32; A61F 2/38; A61F 2/3804; A61F 2/40; A61F 2/4202; A61F 2/44;
(Continued)

(56) References Cited

U.S. PATENT DOCUMENTS

| 4,501,266 A | 2/1985 | McDaniel |
| 5,197,488 A | 3/1993 | Kovacevic |

(Continued)

FOREIGN PATENT DOCUMENTS

| JP | 2008517708 A | 5/2008 |
| WO | WO-03079940 A2 | 10/2003 |

(Continued)

OTHER PUBLICATIONS

"U.S. Appl. No. 12/544,897, Final Office Action dated Apr. 17, 2012", 14 pgs.

(Continued)

*Primary Examiner* — Rene Towa
*Assistant Examiner* — H. Q. Nguyen
(74) *Attorney, Agent, or Firm* — Schwegman Lundberg & Woessner, P.A.

(57) ABSTRACT

Systems, devices, and methods are provided for measuring forces in the space of a knee during surgery. Such forces can be caused by tension in the ligaments of the knee. A femoral member is engaged with a distal femur. While the knee is flexed, partially extended, or fully extended, a force sensor and a gauge shim can be placed in the gap between the femoral member and the tibial plateau to measure the forces therebetween. The force sensor provides an accurate and quantifiable measurement of force, making knee replacement surgery and ligament tension balancing more accurate, standardized and repeatable. The force sensor comprises an elongate housing which comprises a thin force sensing distal portion and a proximal handle portion.

40 Claims, 14 Drawing Sheets

Related U.S. Application Data

(60) Provisional application No. 61/090,535, filed on Aug. 20, 2008.

(51) Int. Cl.
*A61B 17/88* (2006.01)
*A61F 2/32* (2006.01)
*A61F 2/40* (2006.01)
*A61F 2/42* (2006.01)
*A61F 2/44* (2006.01)

(52) U.S. Cl.
CPC ............... *A61F 2/3804* (2013.01); *A61F 2/40* (2013.01); *A61F 2/4202* (2013.01); *A61F 2/44* (2013.01); *A61F 2/4684* (2013.01); *A61F 2002/4666* (2013.01); *A61F 2002/4687* (2013.01)

(58) Field of Classification Search
CPC .................. A61F 2/4657; A61F 2/4684; A61F 2002/4687; A61B 17/88
USPC ................. 606/86 F–105; 600/587, 594–595
See application file for complete search history.

(56) References Cited

U.S. PATENT DOCUMENTS

| | | |
|---|---|---|
| 5,470,354 A | 11/1995 | Hershberger et al. |
| 5,540,696 A | 7/1996 | Booth, Jr. et al. |
| 5,597,379 A | 1/1997 | Haines et al. |
| 5,656,785 A | 8/1997 | Trainor et al. |
| 5,733,292 A | 3/1998 | Gustilo et al. |
| 5,800,438 A | 9/1998 | Tuke et al. |
| 5,860,980 A | 1/1999 | Axleson, Jr. et al. |
| 5,911,723 A | 6/1999 | Ashby et al. |
| 6,022,377 A | 2/2000 | Nuelle et al. |
| 6,575,980 B1 | 6/2003 | Robie et al. |
| 6,758,850 B2 | 7/2004 | Smith et al. |
| 7,104,996 B2 | 9/2006 | Bonutti |
| 7,442,196 B2 | 10/2008 | Fisher et al. |
| 7,578,821 B2 | 8/2009 | Fisher et al. |
| 8,211,041 B2 | 7/2012 | Fisher et al. |
| 2005/0209605 A1 | 9/2005 | Grimm et al. |
| 2005/0240196 A1 | 10/2005 | Davis et al. |
| 2005/0267485 A1 | 12/2005 | Cordes et al. |
| 2006/0241569 A1 | 10/2006 | Disilvestro |
| 2007/0219559 A1 | 9/2007 | Heavener et al. |
| 2007/0232959 A1 | 10/2007 | Couture et al. |
| 2013/0103038 A1 | 4/2013 | Fischer et al. |

FOREIGN PATENT DOCUMENTS

| | | | |
|---|---|---|---|
| WO | WO 2005/037121 A2 | 4/2005 | |
| WO | WO 2005/089681 A2 | 9/2005 | |
| WO | WO-2005089681 A1 | 9/2005 | |
| WO | WO 2006/047005 A2 | 5/2006 | |

OTHER PUBLICATIONS

"U.S. Appl. No. 12/544,897, Non Final Office Action dated Mar. 6, 2012", 10 pgs.
"U.S. Appl. No. 12/544,897, Notice of Allowance dated May 2, 2012", 5 pgs.
"U.S. Appl. No. 12/544,897, Response filed Feb. 17, 2012 to Restriction Requirement dated Jan. 17, 2012", 2 pgs.
"U.S. Appl. No. 12/544,897, Response filed Mar. 26, 2012 to Non Final Office Action dated Mar. 6, 2012", 12 pgs.
"U.S. Appl. No. 12/544,897, Response filed Apr. 19, 2012 to Final Office Action dated Apr. 17, 2012", 10 pgs.
"U.S. Appl. No. 12/544,897, Restriction Requirement dated Jan. 17, 2012", 8 pgs.
"U.S. Appl. No. 13/709,491, Preliminary Amendment dated Dec. 10, 2012", 3 pgs.
"Australia Application Serial No. 591206, Examiner Report dated Mar. 21, 2012", 2 pgs.
"European Application Serial No. 09808836.2, Office Action dated May 24, 2011", 2 pgs.
"International Application Serial No. PCT/EP2004/011481, International Search Report dated Sep. 2, 2005", 3 pgs.
"International Application Serial No. PCT/US2009/054518, International Preliminary Report on Patentability dated Feb. 22, 2011", 9 pgs.
"International Application Serial No. PCT/US2009/054518, Written Opinion dated Oct. 15, 2009", 8 pgs.
"Japanese Application Serial No. 2011-524007, Voluntary Amendment filed Aug. 29, 2012", 8 pgs.
International Search Report dated Jan. 13, 2010 for PCT/US09/62846.
Written Opinion of the International Search Authority dated Jan. 13, 2010 for PCT/US09/62846.
Eckhoff, D.G. et al., "Three-Dimensional Morphology and Kinematics of the Distal Part of the Femur Viewed in Virtual Reality", *Journal of Bone & Joint Surgery*, vol. 85-A, Supplement 4, 2003, 97-104.
Mihalko, W.H. et al., "Comparison of Ligament-Balancing Techniques During Total Knee Arthroplasty", *Journal of Bone & Joint Surgery*, vol. 85-A, Supplement 4, 2003, 132-135.
Murray, D.G., "Variable Axis Total Knee Surgical Technique," Howmedica Surgical Techniques, 1977 Howmedica, Inc. pp. 2-7.
Ries, M.D. et al., "Soft-Tissue Balance in Revision Total Knee Arthroplasty," *Journal of Bone & Joint Surgery*, vol. 85-A, Supplement 4, 2003, pp. 38-42.
International Search Report corresponding to International Application No. PCT/US2009/054518, dated Oct. 15, 2009.
"Japanese Application Serial No. 2011-524007, Office Action dated Aug. 29, 2013", 11 pgs.
"New Zealand Application Serial No. 201001389, Response filed Mar. 19, 2013 to Office Action dated Mar. 21, 2012", 21 pgs.
"New Zealand Application Serial No. 591206, Examiner Report dated Apr. 4, 2013", 2 pgs.
"New Zealand Application Serial No. 591206, Response filed Jun. 13, 2013 to Examiner Report dated Apr. 4, 2013", 10 pgs.

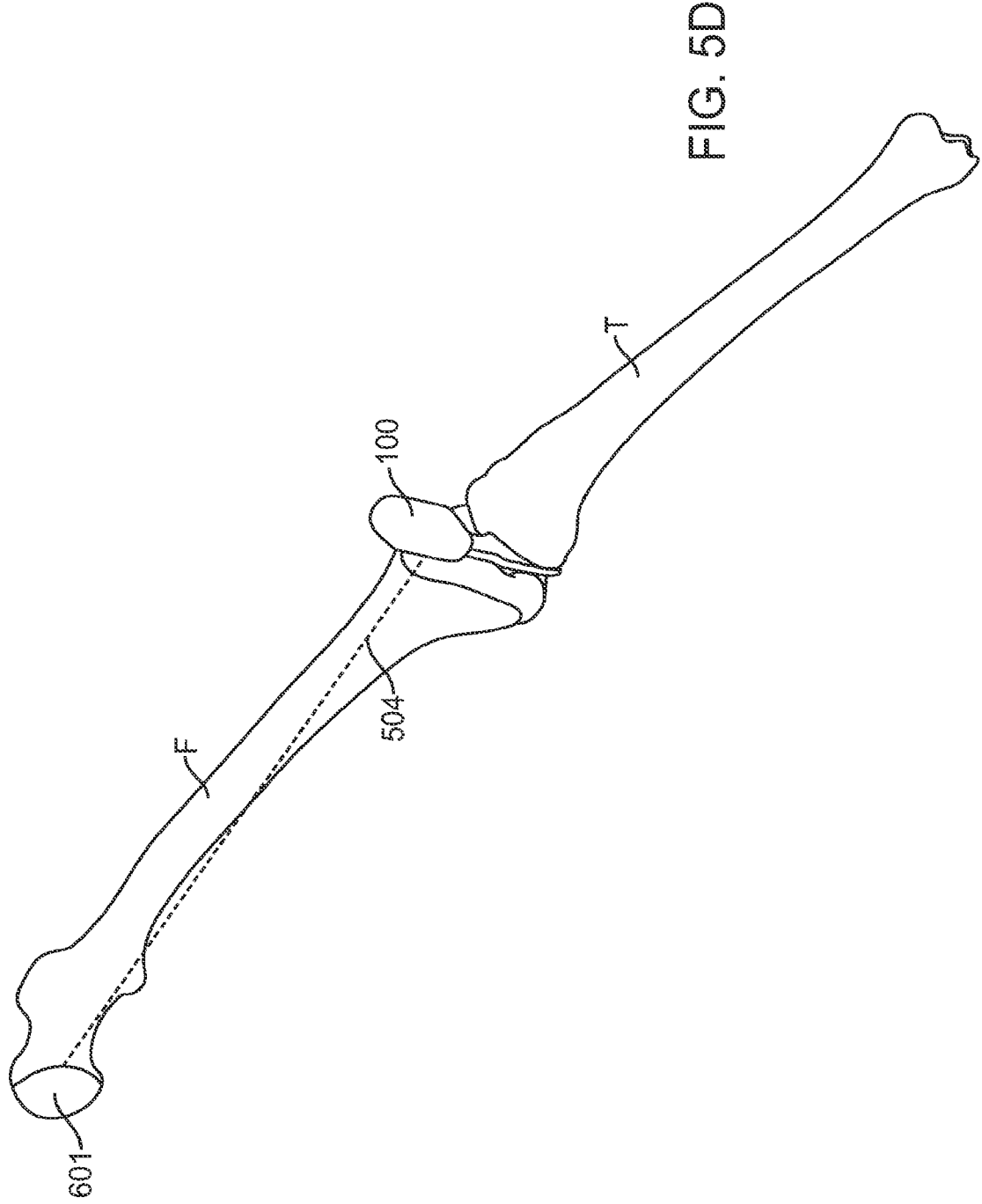

SENSING FORCE DURING PARTIAL AND TOTAL KNEE REPLACEMENT SURGERY

CROSS-REFERENCE TO RELATED APPLICATIONS

The present application is a divisional of, and claims the benefit of priority of U.S. application Ser. No. 12/544,897, filed Aug. 20, 2009, which is a non-provisional of, and claims the benefit of priority under 35 U.S.C. Section 119(e) of, U.S. Provisional Application No. 61/090,535, filed Aug. 20, 2008, the entire contents of which are incorporated herein by reference.

BACKGROUND OF THE INVENTION

The present invention relates generally to medical surgical devices, systems, and methods. More specifically, the invention relates to devices, systems and methods for enhancing knee surgery including measuring forces in flexion and/or extension gap(s) during knee arthroplasty.

The knee is generally defined as the point of articulation of the femur with the tibia. Structures that make up the knee include the distal femur, the proximal tibia, the patella, and the soft tissues within and surrounding the knee joint, the soft tissues including the ligaments of the knee. The knee is generally divided into three compartments: medial (the inside part of the knee), lateral (the outside part of the knee), and patellofemoral (the joint between the kneecap and the femur). The medial compartment comprises the medial joint surfaces of the femur, tibia, and the meniscus wedged therebetween. The lateral compartment comprises the lateral joint surfaces of the femur, tibia, and the meniscus wedged therebetween. The patellofemoral compartment comprises the joint between the undersurface of the kneecap or patella and the femur. Four ligaments are especially important in the stability, alignment and functioning of the knee—the anterior cruciate ligament, the posterior cruciate ligament, the medial collateral ligament, and the lateral collateral ligament. In an arthritic knee, protective cartilage at the point of articulation of the femur with the tibia is often worn away, allowing the femur to directly contact the tibia. This bone-on-bone contact can cause significant pain, discomfort, and disability for a patient and will often necessitate knee replacement or knee arthroplasty.

Knee arthroplasty involves replacing the diseased and painful joint surface of the knee with metal and plastic components shaped to allow natural motion of the knee. Knee replacement may be total or partial. Total knee replacement surgery, also referred to as total knee arthroplasty ("TKA"), involves a total replacement of the distal end of the femur, the proximal end of the tibia, and often the inner surface of the patella with prosthetic parts. Cuts are made on the distal end of the femur and the proximal end of the tibia. Prosthetic parts are then attached. The prosthetic parts create a stable knee joint that moves through a wide range of motion. The replacement of knee structures with prosthetic parts allows the knee to avoid bone-on-bone contact and provides smooth, well-aligned surfaces for joint movement.

In TKA, the distal end of the femur and the proximal end of the tibia are completely removed. Thus, healthy tissue may be removed as well. For patients with worn out cartilage in only one compartment, an alternative to TKA may be partial knee replacement, or unicompartmental knee arthroplasty ("UKA"), an example of which is the Oxford® Partial Knee Replacement procedure. Advantages of UKA compared to TKA include smaller incisions, easier post-op rehabilitation, shorter hospital stay, less blood loss, lower risk of infection, stiffness, and blood clots, and easier revision surgery if necessary.

A challenge in knee replacement surgeries, including both TKA and UKA, is the proper balancing of ligament tension, especially of the medial and lateral collateral ligaments, through the full range of motion of the knee, from a flexed position to a fully extended position. The collateral ligaments, which connect the distal femur and proximal tibia on the medial and lateral sides of the knee, account for much of the stability and movement of the knee. Uneven ligament tension after knee replacement surgery will typically lead to symptoms including joint instability and poor patellar tracking, limited range of motion, impaired function of the knee, and uneven, increased wear and/or loosening of the prosthetic device. These symptoms may often necessitate a repeat surgery. Thus, it is imperative for the short and long-term success of a knee replacement procedure to achieve balanced ligament tension in the knee through the full range of motion of the knee.

Balancing ligament tension during knee replacement surgery is complicated by the fact that the natural knee does not operate like a hinge moving about a single axis. The knee exhibits dynamic rotation of the tibia relative to the femur as the knee moves from its flexed position to its fully extended position and vice versa. Thus, the natural knee exhibits a rotary laxity that allows the tibia to rotate through a limited internal and external arc during knee flexion. Additionally, the femur translates anteriorly and posteriorly as the tibia is being flexed about it, bringing yet another movement variable. Thus, the ligaments of the knee, along with the femur, tibia and patella, create a dynamic bio-mechanism, making ligament tension balancing in TKA surgery challenging. Many articles and studies have been devoted to ligament tension balancing in TKA, such as: Mihalko, W. H. et al., "Comparison of Ligament-Balancing Techniques During Total Knee Arthroplasty," Journal of Bone & Joint Surgery, Vol. 85-A, Supplement 4, 2003, 132-135; Eckhoff, D. G. et al., "Three-Dimensional Morphology and Kinematics of the Distal Part of the Femur Viewed in Virtual Reality, Journal of Bone & Joint Surgery, Vol. 85-A, Supplement 4, 2003, 97-104; and Ries, M. D., et al., "Soft-Tissue Balance in Revision Total Knee Arthroplasty," Journal of Bone & Joint Surgery, Vol. 85-A, Supplement 4, 2003, 38-42.

One technique for balancing collateral ligament tension during a knee replacement procedure involves cutting fibers of one or both ligaments to decrease ligament tension—a technique referred to as "ligament release." A disadvantage of this technique is that the cutting of ligament tissue weakens the ligament(s) and leaves less room for error if future ligament releases or knee replacement procedures are required.

Rather than or in addition to ligament release, the components of a knee prosthesis may be selected and positioned to balance ligament tension. In a typical knee replacement procedure, multiple cuts are made to the distal femur before attaching the femoral component of the prosthesis. Most TKA procedures, for example, involve making distal cuts across the distal end of the femur, anterior and posterior cuts, and angled anterior and posterior chamfer cuts to help secure the femoral component solidly in place. The surgeon attempts to make these femoral bone cuts to achieve a position and orientation of the femoral prosthetic component so as to optimally balance ligament tension through a full range of motion of the knee. However, it is often very challenging to position the femoral bone cuts and femoral prosthetic component to provide ideal ligament tension through the full range of motion of the knee. This is due primarily to the complexity of motion about the knee, as described above, and the difficulty of placing the femoral component so as to maintain desired ligament tension through the full range of motion.

A number of devices and techniques have been described that attempt to facilitate ligament balancing during a TKA procedure. Some techniques, such as those described in U.S. Pat. No. 5,733,292, involve trial prosthesis components which are used after femoral and tibial bone cuts are made to assess ligament tension. Some devices, such as those described in U.S. Patent Application Publication No. 2003/0187452 A1, are used to measure a gap between the distal femur and proximal tibia in extension and to help a surgeon recreate that same gap when the knee is in flexion. Other "gap checking" devices are described in U.S. Pat. No. 6,575,980. Other devices have been developed to help measure an amount of ligament tension or to apply a desired amount of tension to the ligaments. U.S. Pat. No. 4,501,266, for example, describes a knee distraction device for applying a desired amount of tension. Many paddle-like devices have been suggested for applying or measuring tension across a knee joint, such as the devices described in U.S. Pat. Nos. 5,597,379; 5,540,696; 5,800,438; 5,860,980; 5,911,723; and 6,022,377. Other methods and device are described in co-assigned and co-pending U.S. patent application Ser. No. 10/773,608, Ser. No. 10/973,936, and Ser. No. 11/149,944, the contents of which are fully incorporated herein by reference.

The devices described for facilitating ligament balancing during a TKA procedure may also find use in UKA procedures. In certain UKA procedures, for example, the Oxford® Partial Knee Replacement, a surgeon may be provided with a set of shims or feeler gauges, each with a certain thickness. The shims or feeler gauges are used to measure the gap between the distal femur and proximal tibia to facilitate balancing knee tension. Once a side of the distal femur and a complementary side of the proximal tibia has been cut or milled down, the surfaces of the distal femur and proximal tibia may be fitted with template prostheses. With the knee in flexion, the surgeon may measure the thickness of the gap between the femoral and tibial prostheses by placing a shim or feeler gauge into the gap so that "natural tension" in the knee is achieved. "Natural tension" may be achieved when the shim or feeler gauge slides in and out of the gap easily but does not tilt. With the shim or feeler gauge removed, the knee is then extended, for example, in 20 degrees of flexion, and the gap similarly measured. Tension in the knee can be balanced by further cutting or milling off the end of the distal femur so that the gap between the distal femur and proximal tibia is the same when the knee is in flexion as when the knee is extended. The distal femur is further cut or milled based on the difference between the gap size of the knee in flexion and the gap size of the knee extended. For example, if the flexion gap is measured to be 5 mm and the extension gap is measure to be 2 mm, the amount of bone to be milled is 3 mm. This procedure, however, is highly dependent on the subjective "feel" of the surgeon. Thus, there is a need to quantify and standardize the procedure.

For the above reasons, a need exists for improved devices, systems and methods for enhancing knee replacement surgery and specifically for dynamically balancing ligaments during knee replacement to improve range of motion, stability, and patellar tracking of the prosthetic knee joint. Ideally, such devices and methods would allow a surgeon to achieve a desired ligament tension balance before committing to and making final bone cuts to the femur. Such devices would ideally be simple to use in conjunction with existing knee replacement procedures and equipment such as prosthesis templates, measurement guides, cutting guides, and saw blades or burs. At least some of these objectives will be met by the present invention.

BRIEF SUMMARY OF THE INVENTION

Embodiments of the invention provide systems, devices, and methods for measuring forces in the space of a knee during surgery. Such forces can be caused by tension in the ligaments of the knee. A femoral member is engaged with a distal femur. While the knee is flexed, partially extended, or fully extended, a force sensor and a gauge shim can be placed in the gap between the end of the femoral member and the tibial plateau to measure the forces therebetween. The force sensor provides an accurate and quantifiable measurement of force, making knee replacement surgery and ligament tension balancing more accurate, standardized and repeatable. The force sensor comprises an elongate housing which comprises a thin force sensing distal portion and a proximal handle portion. A sensor element is disposed within the thin force sensing distal portion of the elongate housing.

An aspect of the invention provides a system for measuring forces in the space of an anatomical joint. The system comprises a force sensor comprising an elongate housing and a sensor element. The elongate housing comprises a thin force sensing distal portion and a proximal handle portion. The thin force sensing distal portion includes the sensor element. The anatomical joint is often a knee and the forces in the space of the anatomical joint are caused by ligaments adjacent the knee. Alternatively, the anatomical joint may be another joint, for example, an elbow joint, an intervertebral joint, a hip joint, an ankle joint, or shoulder joint. The elongate housing may further comprise a stop portion proximal of the thin distal portion and distal of the proximal handle portion.

In many embodiments, the sensor element comprises a force sensing member. The force sensing member may be selected from the group consisting of piezoelectric sensors, force sensing resistors, force sensing capacitors, strain gages, load cells, pressure sensors, and other force sensors. The visual display may be incorporated into the same housing as the sensor, typically being hard-wired or may be coupled wirelessly with the processor. In some embodiments, the thin distal portion of the elongate housing comprises a wide distal region and a thin proximal region. The force sensing member of the sensor element is disposed within the wide distal region of the elongate housing. The sensor element may further comprise a distal wiring portion extending proximally of the force sensing member.

In many embodiments, the system further comprises a processor and a visual display. The processor is coupled with the sensor element for processing sensed force data into usable data for providing to a user. The visual display is coupled with the processor and adapted to display the usable data by any one of various graphical or numerical interfaces including digital screens, Liquid Crystal Displays (LCD), Light Emitting Diodes (LED), etc. The visual display is attached to the proximal handle portion. The visual display comprises a plurality of different colored lights. A light is illuminated in response to discrete incremental changes in force applied to the sensor element. Each illuminated light corresponds to an increase of force applied to the sensor. The visual display comprises a plurality of different colored lights. Each light is separately illuminated in response to a different predetermined force detected by the sensor element.

The visual display may be wirelessly coupled with the processor through a wireless connection such as an infrared connection, a radiofrequency connection, a BlueTooth® connection, a Z-Wave connection, and a Zigbee® connection. In some embodiments, the system further comprises tangible media coupled to the at least one of the processor and visual display. The tangible media is configured to store a value of the measured force.

In many embodiments, the system further comprises at least one gauge shim. The at least one gauge shim is concave and has a condylar contact area, typically defined by a spherically concave (i.e. curved inward) region as described below. In some embodiments, a length of the thin distal force sensing portion may match a length of the condylar contact area of the at least one gauge shim. In some embodiments, the elongate bar may have a flat first side and a tapered second side opposite the first side. The flat first side may be adapted to match the at least one gauge shim. The tapered second side may be tapered towards a distal end of the elongate bar.

In many embodiments, the stop portion is thicker than the thin distal portion. In many embodiments, the stop portion is attached perpendicular to the distal end of the thin portion to limit the insertion distance of the handheld force sensor into an anatomical joint. In many embodiments, the proximal handle portion is thicker than the thin distal force sensing portion.

In many embodiments, the system further comprises a light source attached to the proximal handle portion. The light source is configured to emit a line of visible light across the force sensing pad toward the anterior portion of the distal femur so as to capture the midline of the condylar center of the femoral component when the force sensor is disposed in a gap between a femoral member and a tibial plateau with the knee in approximately 90 degrees of flexion. In many embodiments, the light indicates rotational alignment with the condylar center of the femoral component during flexion. In other embodiments, the system further comprises a light source attached to the proximal handle portion. The light source is configured to emit a line of visible light across the force sensing pad toward the hip so as to capture the location of the hip center when the force sensor is disposed in a gap between a femoral member and a tibial plateau with the knee in extension. In many embodiments, the light is a laser.

Another aspect of the invention provides a handheld device for measuring forces in the space of an anatomical joint. The device comprises an elongate housing and a sensor element. The elongate housing comprises a thin force sensing distal portion and a proximal handle portion. The thin force sensing distal portion includes the sensor element. The anatomical joint is often a knee and forces in the space of the anatomical joint are caused by ligaments adjacent the knee. Alternatively, the anatomical joint may be another joint, for example, an elbow joint, an intervertebral joint, a hip joint, an ankle joint, or shoulder joint. The elongate housing may further comprise a stop portion proximal of the thin distal portion and distal the proximal handle portion.

In many embodiments, the sensor element comprises a force sensing member. The force sensing member may be selected from the group consisting of piezoelectric sensors, force sensing resistors, force sensing capacitors, strain gages, load cells, pressure sensors, and other force sensors. In many embodiments, the thin distal portion of the elongate housing comprises a wide distal region and a thin proximal region. The force sensing member includes the sensor element. The sensor element may further comprises a distal wiring portion extending proximally of the force sensing member.

In many embodiments, the handheld device further comprises a processor coupled with the sensor element for processing sensed force data into usable data for providing to a user and a visual display coupled with the processor and adapted to display the usable data. The device may further comprise a power source coupled with the sensor element and the processor.

In many embodiments, the elongate housing has a flat first side and a tapered second side opposite the first side. The tapered second side may be tapered towards a distal end of the elongate housing.

In many embodiments, the stop portion is thicker than the thin distal force sensing portion. In many embodiments, the proximal handle portion is thicker than the thin distal portion.

Another aspect of the invention provides a method for measuring forces in the space of a knee during surgery. The method comprises placing a force sensor in a gap between the distal femur and the proximal tibia and measuring a force exerted by the ligaments of the knee on the force sensing portion of the force sensor. In many embodiments, the method comprises placing a force sensor in a gap between the distal femur and the proximal tibia comprises placing a distal portion of the force sensor over the proximal tibial plateau. In many embodiments, the force sensor is placed in the gap and the force is measured when the knee is in flexion. In many embodiments, the force sensor is placed in the gap and the force is measured when the knee is partially extended. In many embodiments, the force sensor is placed in the gap and the force is measured when the knee is in full extension. In many embodiments, the force sensor in the gap along with a gauge shim is moveably coupled to the force sensor to measure the forces in the gap that has been increased due to bone being resected from one of the proximal tibia or distal femur. In many embodiments, the natural tension in the ligaments of the knee is achieved when the combination of the thickness of the moveably coupled gauge shim and the thickness of the force sensor provide a force measurement indicating the ligaments of the knee have toned to an acceptable tension.

In many embodiments, the method further comprises processing data based on the measured force into usable data for providing to a user and displaying the usable data on a visual display. In many embodiments, the method comprises placing the force sensor in a gap a multitude of times in a repeatable fashion so as to align the force sensor to one of identified anatomical or surgical landmarks or devices. In many embodiments, the method further comprises placing the force sensor in a gap a multitude of times entering from the anterior aspect of the gap and stopping at the same position in the posterior aspect of the gap. In many embodiments, the method further comprises stopping at the same posterior aspect of the gap by abutting the force sensor against one of identified anatomical or surgical landmarks or devices. In many embodiments, the method comprises placing the force sensor in a gap a multitude of times entering from the anterior aspect of the gap and stopping at the same position in the posterior aspect of the gap and rotationally aligning the force sensor in the same orientation relative to one of anatomical or surgical landmarks, or devices.

In many embodiments, the method further comprises rotationally aligning the force sensor in the same orientation relative to one of anatomical or surgical landmarks or devices by visualizing a line or beam of light upon or cast from the force sensor. In many embodiments, the method further comprises storing the usable data on a tangible medium coupled to the visual display. In many embodiments, the method includes measuring a force exerted by the ligaments of the knee on the force sensing portion of the force sensor by transmitting a voltage to a sensor element of the thin force sensing portion of the force sensor, measuring the voltage after it has passed through the sensor element, determining a percentage of the voltage passed through the sensor element relative to the voltage transmitted to the sensor element and deriving the measured force from the percentage.

Another aspect of the invention provides a method for measuring forces in the space of an anatomical joint during surgery. The anatomical joint comprises a first bone having a first end and a second bone having a second end opposing the first end. A prosthesis is engaged with the first end of the first bone. A force sensor is placed in a gap between the prosthesis and the second end of the second bone. A measurement is taken of a force exerted between the first end of the first bone and the second end of the second bone against one another with a force sensing portion of the force sensor. The force sensor is removed from the gap. Placing the force sensor in the gap comprises placing a distal portion of the force sensor over the second end of the second bone. In many embodiments, the method further comprises placing a gauge shim in the gap. In many embodiments, the method further comprises processing data based on the measured force into usable data for providing to a user and displaying the usable data on a visual display.

In many embodiments, the method further comprises storing the usable data on a tangible medium coupled to the visual display. In many embodiments, measuring the force comprises transmitting a voltage to a sensor element of the force sensing portion of the force sensor, measuring the voltage after it has passed through the sensor element, determining a percentage of the voltage passed through the sensor element relative to the voltage transmitted to the sensor element and deriving the measured force from the percentage.

The anatomical joint for which such force is measured may be a knee joint, an elbow joint, an intervertebral joint, a hip joint, an ankle joint, or a shoulder joint.

BRIEF DESCRIPTION OF THE DRAWINGS

FIG. 5D shows a perspective view of a handheld force sensor deployed in the extension gap with the laser beam activated including a medial view of the hip center location.

DETAILED DESCRIPTION OF THE INVENTION

The following exemplary embodiments of systems, devices and methods will be described in the context of sensing force during partial and total knee replacement surgery. This is intended to be for illustrative purposes only and one of ordinary skill in the art will recognize that the systems, devices and methods disclosed herein may be used in a number of other applications and therefore are not limited to knee surgery. The features and advantages will become apparent upon reading the following detailed description and referring to the accompanying drawings in which like numbers refer to like parts throughout.

Figure 1A:
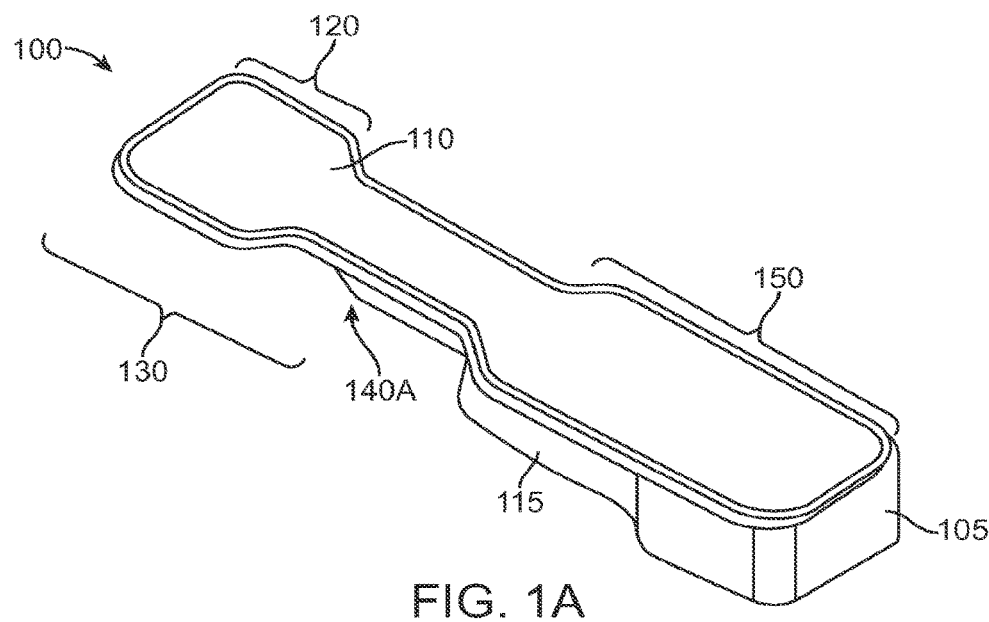
FIG. 1A shows a perspective view of a handheld force sensor according to embodiments of the invention.
Figure 1B:
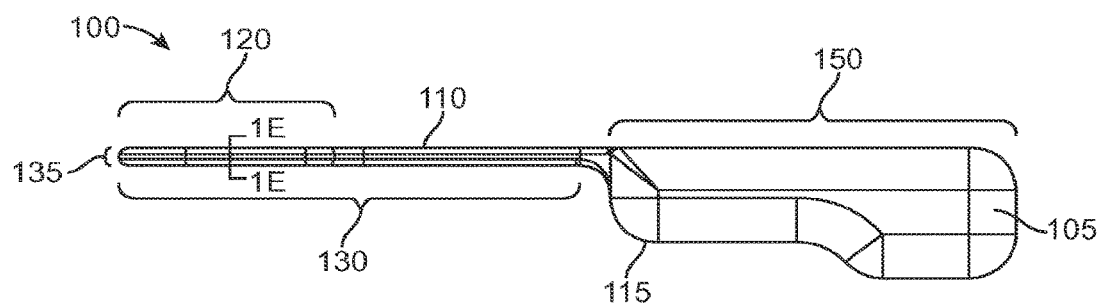
FIG. 1B shows a side view of the force sensor of FIG. 1A.
Figure 1C:
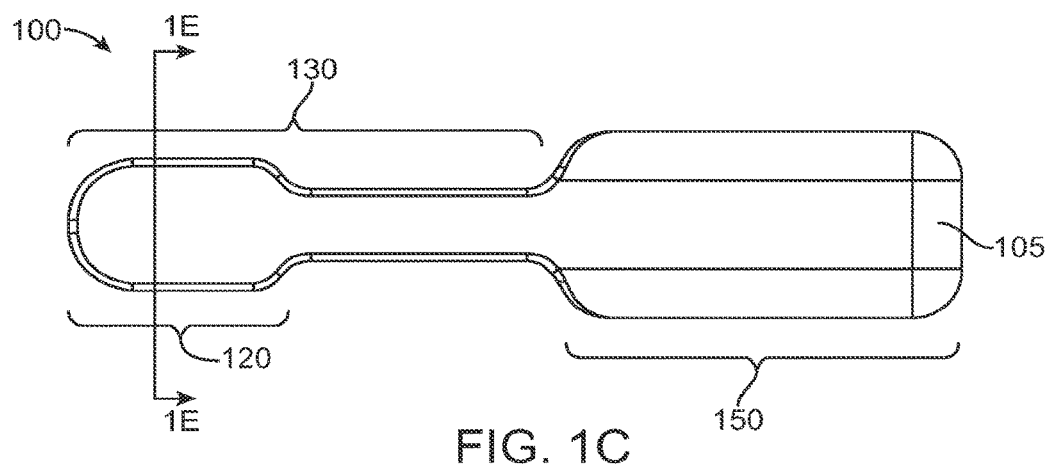
FIG. 1C shows a top view of the force sensor of FIG. 1A.
Figure 1D:
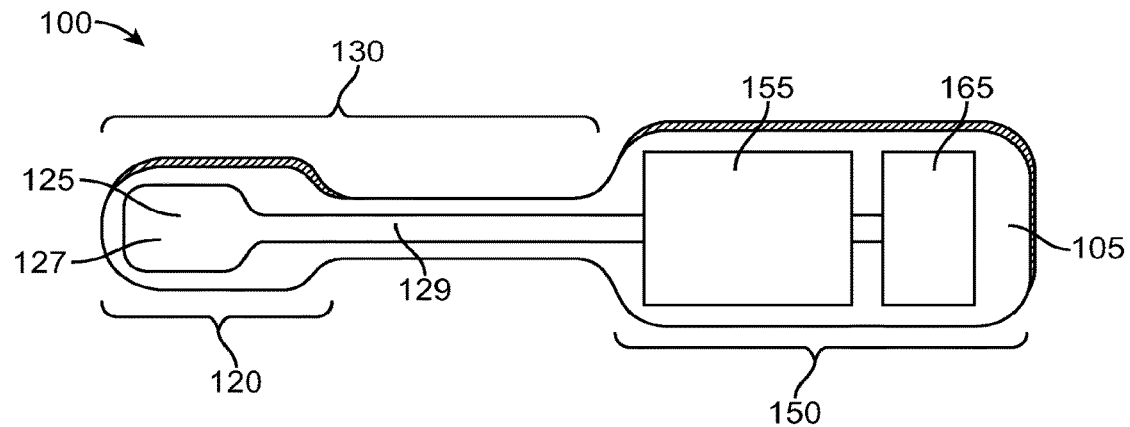
FIG. 1D shows a cross section of the force sensor of FIG. 1A as viewed from the top.
Figure 1E:
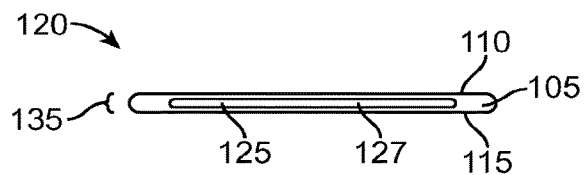
FIG. 1E shows a cross section of a distal portion of the force sensor of FIG. 1A.
Figure 1F:
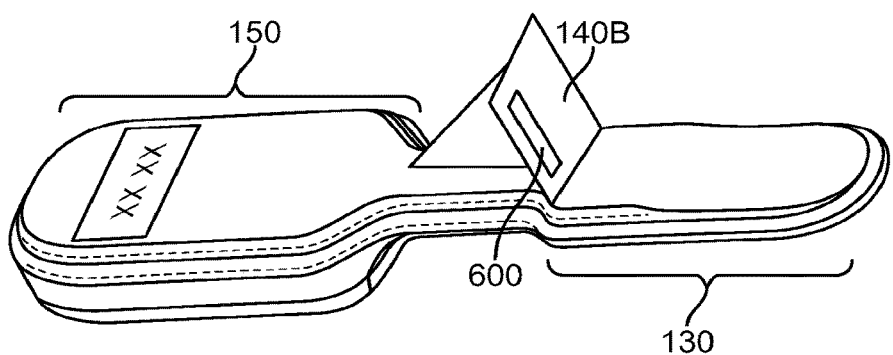
FIG. 1F shows a perspective view of a stop portion of a handheld force sensor according to embodiments of the invention.

FIGS. 1A-1F show a handheld force sensor 100 according to embodiments of the invention. FIG. 1A shows a perspective view of force sensor 100. FIG. 1B shows a side view of force sensor 100. FIG. 1C shows a top view of force sensor 100. FIG. 1D shows a cross section of force sensor 100 as viewed from the top down. FIG. 1E shows a cross section of a distal portion of force sensor 100 as viewed from the front. FIG. 1F shows a perspective view of a stop portion 140B of a handheld force sensor 100 according to embodiments of the invention.

Force sensor 100 comprises an elongate housing 105 having a flat top surface 110 and a tapered bottom surface 115. Tapered bottom surface 115 results in force sensor 100 being generally thicker towards the proximal end of elongate housing 105. Force sensor 100 comprises a thin distal portion 130 with a wide distal force sensing portion 120, and a handle portion 150. The thickness 135 of thin distal portion 130 may be very thin, for example, in the range from about 1 mm to 4 mm, typically 3 mm. Thin distal portion 130 may have a size matching that of the medial compartment or lateral compartment of a knee. Force sensor 100 may further comprise a stop portion 140A or 140B proximal of distal force sensing portion 120. Stop portion 140A is thicker than force distal sensing portion 120. Handle portion 150 may be thicker than both distal sensing portion 120 and stop portion 140A. Alternatively, the stop portion 140B, shown in FIG. 1F, may be configured in a "backstop" configuration. In any configuration, the stop portion limits the insertion distance of the handheld force sensor into an anatomical joint. The stop portion prevents differing anterior/posterior insertion positions because the condylar surface repeatedly fits into the same position on the force sensing pad. The force sensor may be placed in the anatomical joint gap a multitude of times at the same position by abutting the stop against a surgical landmark, such as the femur, and/or a device, such as the femoral component. The "backstop" configuration of stop portion 140B may be made of a transparent material and/or have an opening 600 to allow light to pass through.

FIG. 1D shows a cross section of handheld force sensor 100 as viewed from the top down. Sensor element 125, circuitry or processor 155, and power source 165, for example, a battery, are disposed within elongate housing 105. Sensor element 125 is disposed within thin distal portion 130. As shown in FIG. 1D, processor 155 and power source 165 are disposed within handle portion 150. However, processor 155 and power source 165 may be located outside of elongate housing 105 and may be coupled with force sensor 100 through a wired or wireless connection. Sensor element 125 comprises a force sensing pad or member 127. Force sensing member 127 may have any suitable shape, size, and configuration. In the embodiment shown in FIG. 1D, force sensing member 127 includes a distal force sensing portion 120. The force sensing member 127 may or may not be entirely disposed within the distal force sensing portion 120, for example. Force sensing member 127 may comprise a layer of pressure or force sensing material. Any suitable pressure or force sensing material or combination of materials may be used to form force sensing member 127. Some examples that may be used include, but are not limited to piezoelectric sensors, force sensing resistors, force sensing capacitors, strain gauges, load cells, other pressure sensors and other force sensors.

Sensor element 125 further comprises distal wiring 129 extending distally from force sensing member 127. Distal wiring 129 is disposed at least partially within thin distal portion 130. Sensor element 125 can be coupled to processor 155 through distal wiring 129. Force sensing member 127 can sense pressure or force exerted thereon and distal wiring 129 may send electrical signals representative of the sensed force or pressure. Processor 155 processes these signals into usable data for providing to a user such as a surgeon. For example, usable data may be provided to a surgeon through a visual display coupled with processor 155. The visual display may be coupled with processor 155 through a wired or wireless connection. Wired connections may comprise, for example, a cable connection, an Ethernet connection, a USB connection, and the like. Wireless connections may comprise, for example, an infrared connection, a radiofrequency connection, a BlueTooth® connection, a Z-Wave connection, a Zigbee® connection, and the like. Power source 165 may be coupled to and provide power to sensor element 125 and processor 155.

Figure 4A:
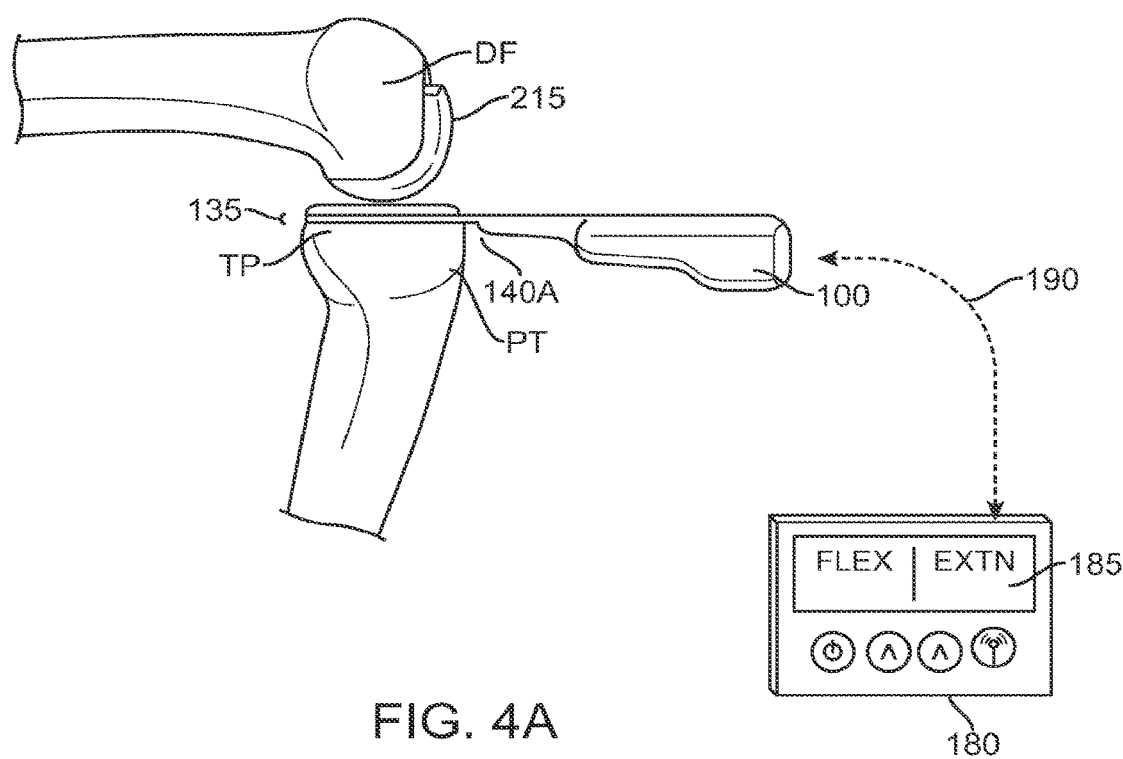
FIGS. 4A-4C show the balancing of knee ligament tension in a partial knee replacement procedure using the force sensor of FIG. 1A.
Figure 4B:
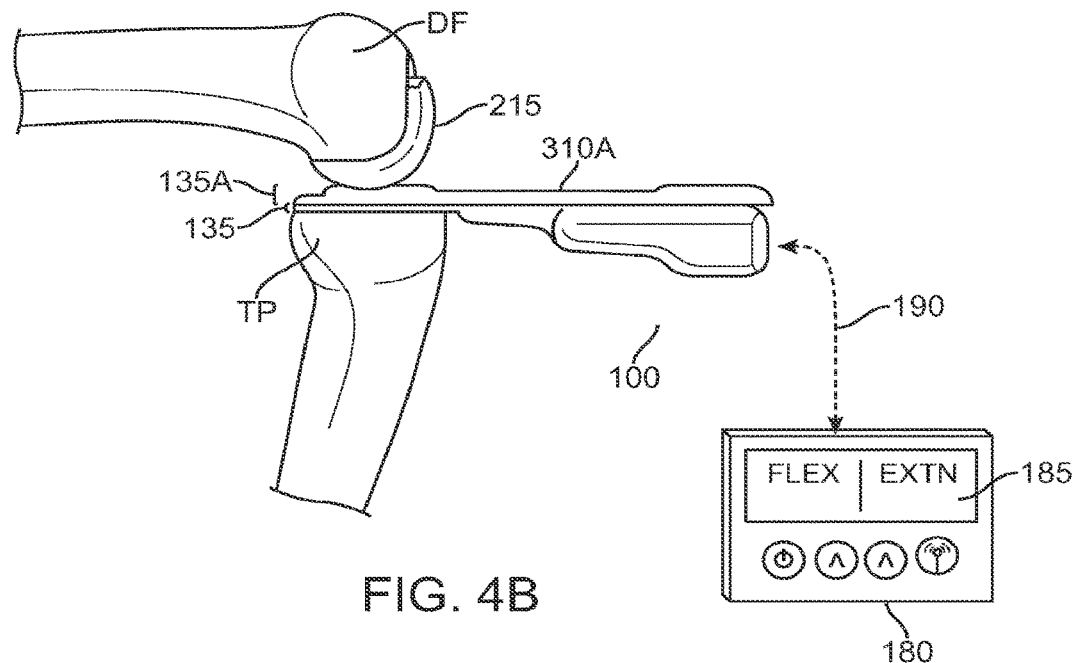
Figure 4C:
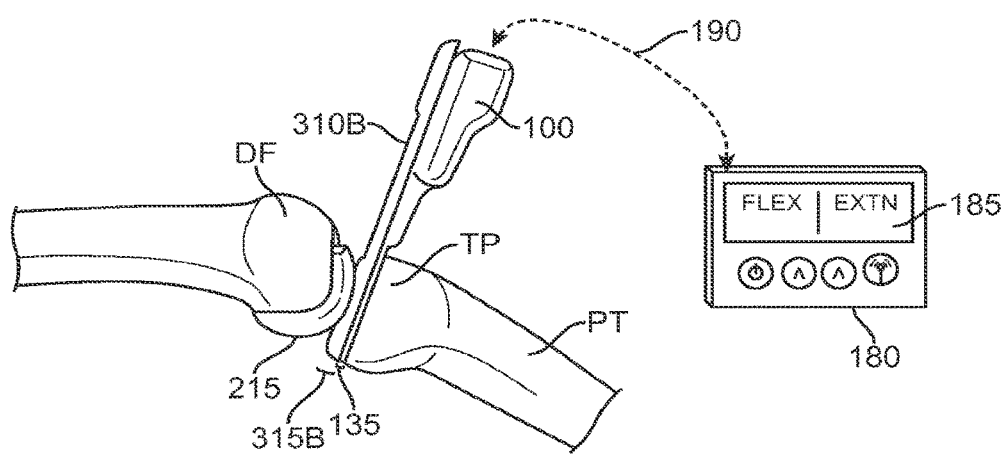
Figure 4D:
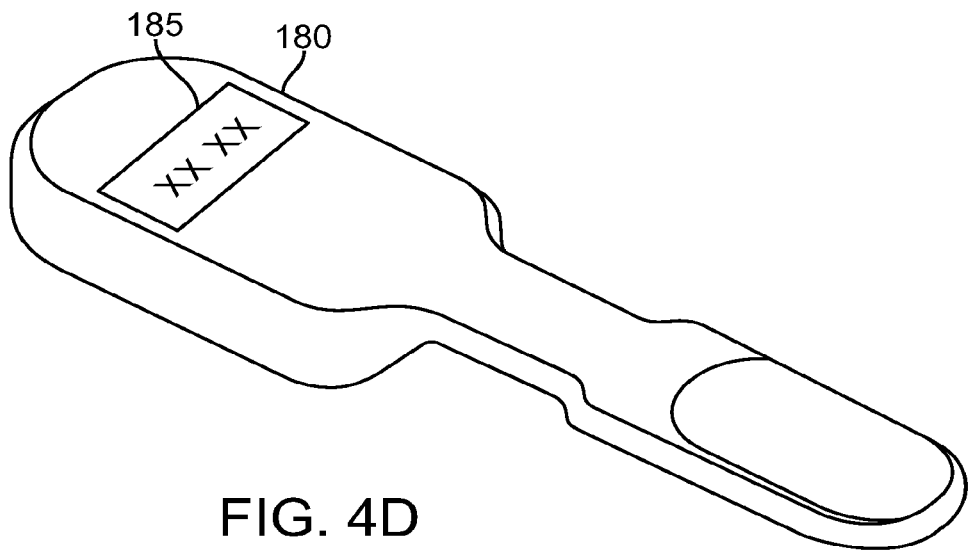
FIGS. 4D-4E show alternative embodiments of the handheld force sensor visual display.
Figure 4E:
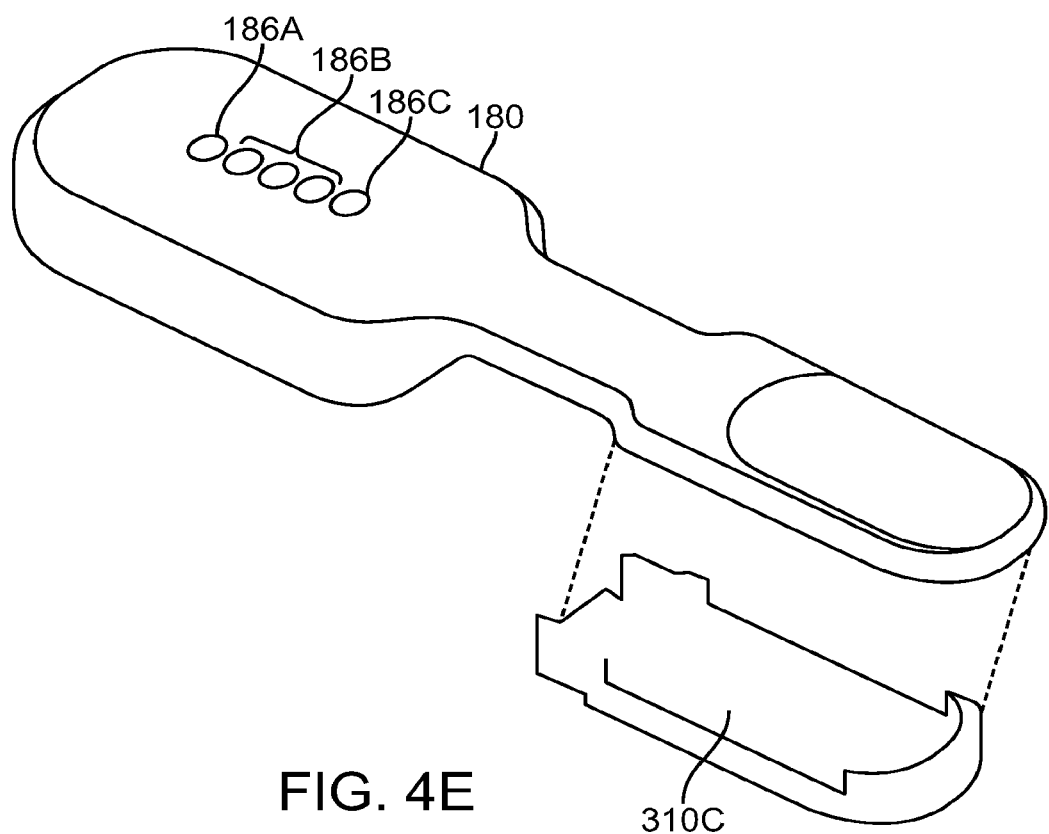

As shown in FIGS. 4D-4E the data may be displayed numerically, visually, or by a code (e.g. green light indicates acceptable force, yellow light indicates marginally acceptable force, red light indicates unacceptable force). The device identifies a functional force value in the joint space in more than one position throughout the range of motion. This enables the physician to surgically adjust the reconstructed joint space to closely approximate natural joint movement and function. The surgeon uses the display as feedback to adjust the joint space by additional milling and/or adjusting the augment thickness, for example.

Sensor element 125 may comprise any of a number of suitable pressure and/or force sensors. In an exemplary embodiment, a known voltage is transmitted to force sensing member 127, the voltage or current out of force sensing member 127 is measured, and a percentage of the voltage leaving force sensing member 127 to the known voltage is calculated. From this percentage, pressure and/or force can be calculated. An analog signal representing the pressure and/or force can be converted to a digital signal with an analog-to-digital (A/D) convertor, and the A/D converter can provide the digital signal to a look-up table that determines a display value (or values) representing the pressure and/or force. A user may use the display value as an absolute number. The A/D converter, as well as any additional processing modules for processing sensed data into usable data may all be housed in a single processor such as processor 155. Alternative methods for sensing and displaying sensed data are also contemplated.

Figure 2B:
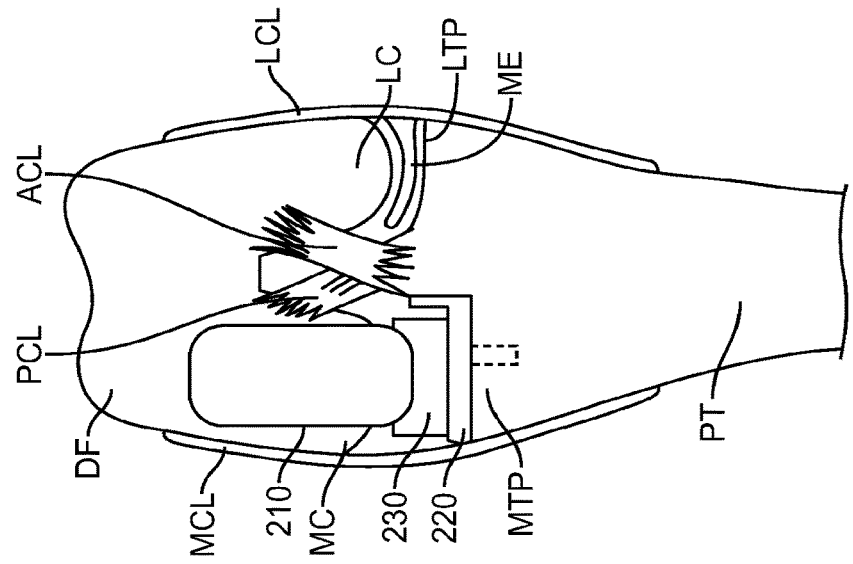
FIGS. 2A and 2B show a knee with a unicompartmental or partial knee replacement.
Figure 2A:
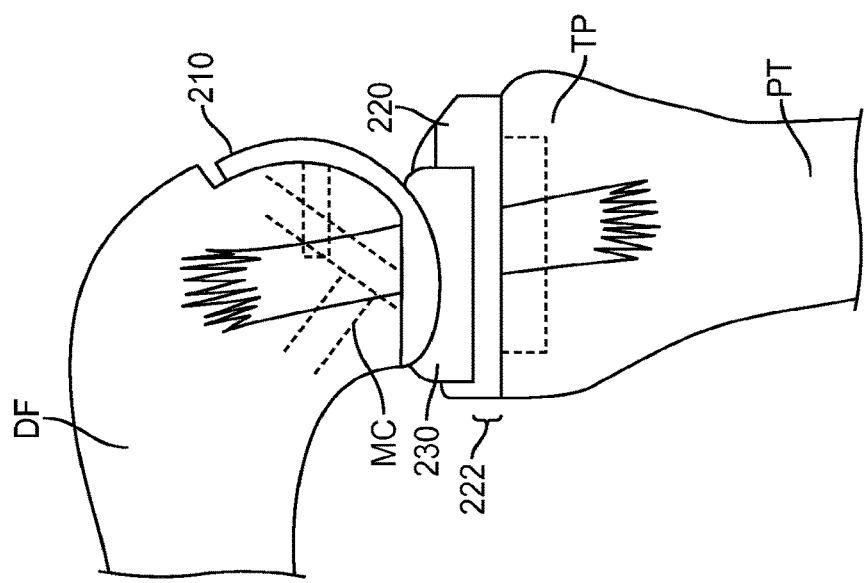

Referring to FIGS. 2A and 2B, embodiments of the invention may find use for partial knee replacement surgery procedures, also known as unicompartmental knee arthroplasty ("UKA"), an example of which is the Oxford® Partial Knee Replacement procedure. FIGS. 2A and 2B show a left knee in flexion and having a knee prostheses in the medial compartment. The knee comprises the distal femur DF and proximal tibia PT as well as knee ligaments, including the anterior cruciate ligament ACL, posterior cruciate ligament PCL, medial collateral ligament MCL, and lateral collateral ligament LCL. In some cases of arthritic or otherwise damaged knees, only one compartment of the knee contains damaged tissue or is otherwise afflicted and requires replacement. In the exemplary UKA procedure shown by FIGS. 2A and 2B, cartilage on the medial condyle MC and on the medial tibial plateau MTP has been worn down (i.e. damaged). Thus, there is painful and debilitating bone-on-bone contact between the distal femur and tibial plateau TP in the medial compartment of the right knee. The lateral condyle LC and lateral tibial plateau LTP remain healthy (i.e. undamaged). The medial condyle MC and medial end of the distal femur DF are cut or milled down and fit with a femoral prosthesis 210. Femoral prosthesis 210 covers the cut surfaces of the medial condyle MC and medial end of the distal femur DF. The bone on medial tibial plateau MTP is cut or milled down and fit with a tibial prosthesis 220 having a thickness 222, for example, a thickness of 3 mm. An artificial bearing surface 230 is placed between femoral prosthesis 210 and tibial prosthesis 230. In other exemplary UKA procedures, the lateral compartment of the left knee and/or a medial or lateral compartment in the right knee may require replacement and be similarly replaced. In any case, the cuts made to the medial or lateral femoral posterior condyle, medial or lateral end of the distal femur, and the medial or lateral tibial plateau must be very precise and properly sized so that tension in the knee ligaments, especially the medial collateral ligament MCL and the lateral collateral ligament LCL, is balanced and the knee is stable and properly aligned through the complete range of motion of the knee, from full flexion to full extension. As used herein, "flexion" refers to bending the knee joint to result in a decrease of angle (i.e. moving the lower leg toward the back of the thigh). As used herein, "extension" refers to straightening the knee joint to result in an increase of angle (i.e. moving the leg away from the back of the thigh).

Figure 2C:
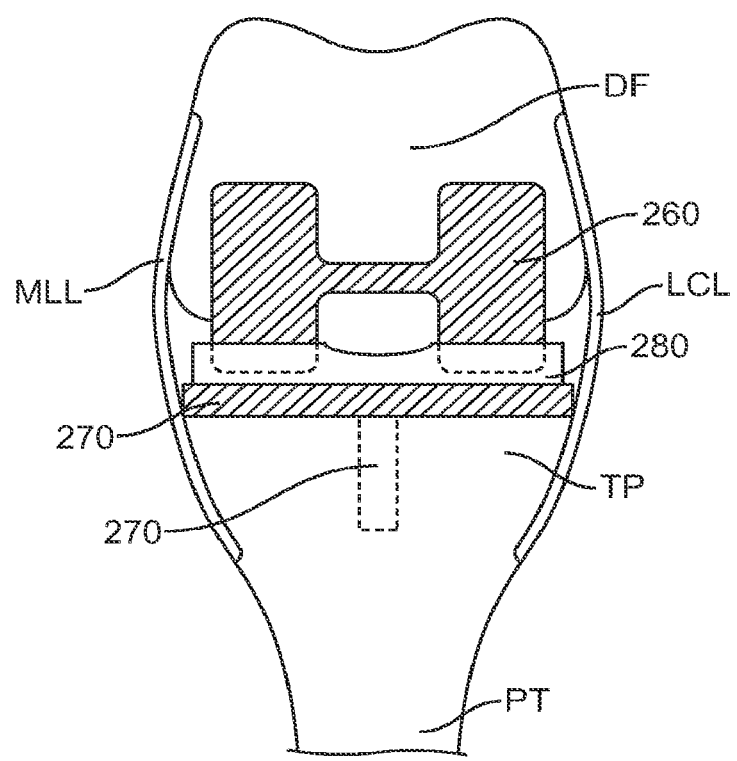
FIG. 2C shows a knee with a total knee replacement.

Referring to FIG. 2C, embodiments of the invention can also find use for total knee replacement surgery procedures, also known as total knee arthroplasty ("TKA"). FIG. 2C shows a front view of a left knee fit with a prosthetic knee. The patella, cruciate ligaments and menisci are not shown. Cartilage on the medial condyle MC, lateral condyle LC, medial tibial plateau MTP, and lateral tibial plateau LTP has been damaged. Thus, there is painful and debilitating bone-on-bone contact between the distal femur and tibial plateau TP in the left knee. In an exemplary TKA procedure, the femoral condyle and end of the distal femur DF have been cut or milled down and fit with a full femoral prosthesis 260. Full femoral prosthesis 260 covers the cut surfaces of the femoral condyle and end of the distal femur DF. The bone on the tibial plateau TP is cut or milled down and fit with a full tibial prosthesis 270. A full artificial bearing surface 280 is placed between full femoral prosthesis 260 and full tibial prosthesis 270. The cuts made to the femoral condyle and the tibial plateau TP must be very precise and properly sized so that tension in the knee ligaments, especially the medial collateral ligament MCL and the lateral collateral ligament LCL, are balanced and the knee and stable and properly aligned through the complete range of motion of the knee, from full flexion to full extension.

Figure 3A:
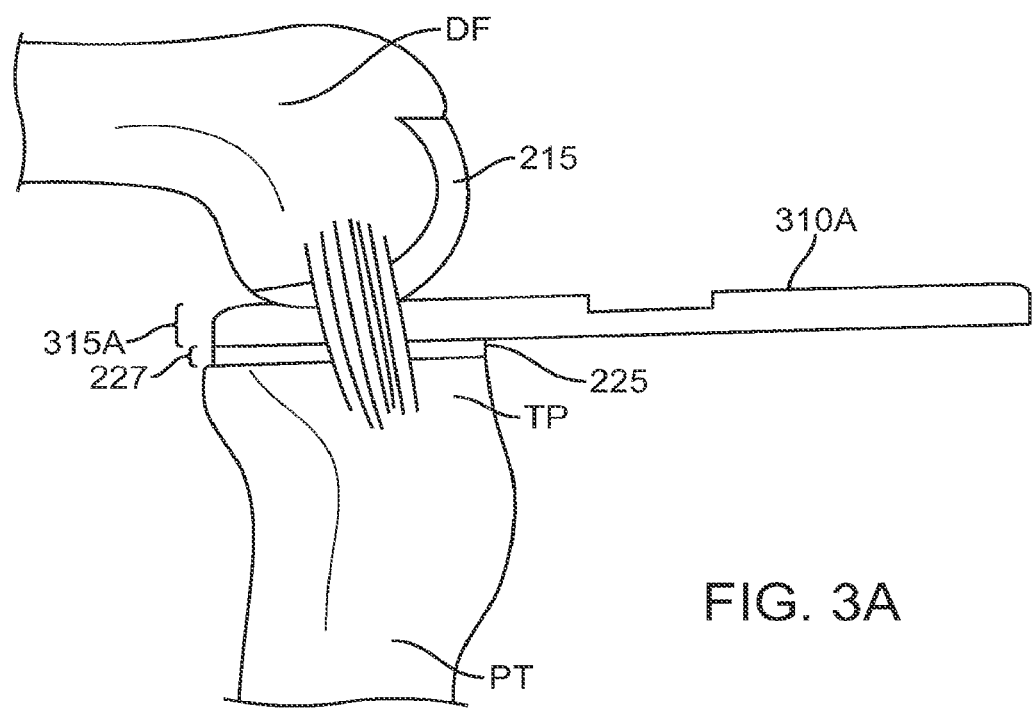
FIGS. 3A and 3B show the balancing of knee ligament tension in a partial knee replacement procedure during flexion and extension, respectively.
Figure 3B:
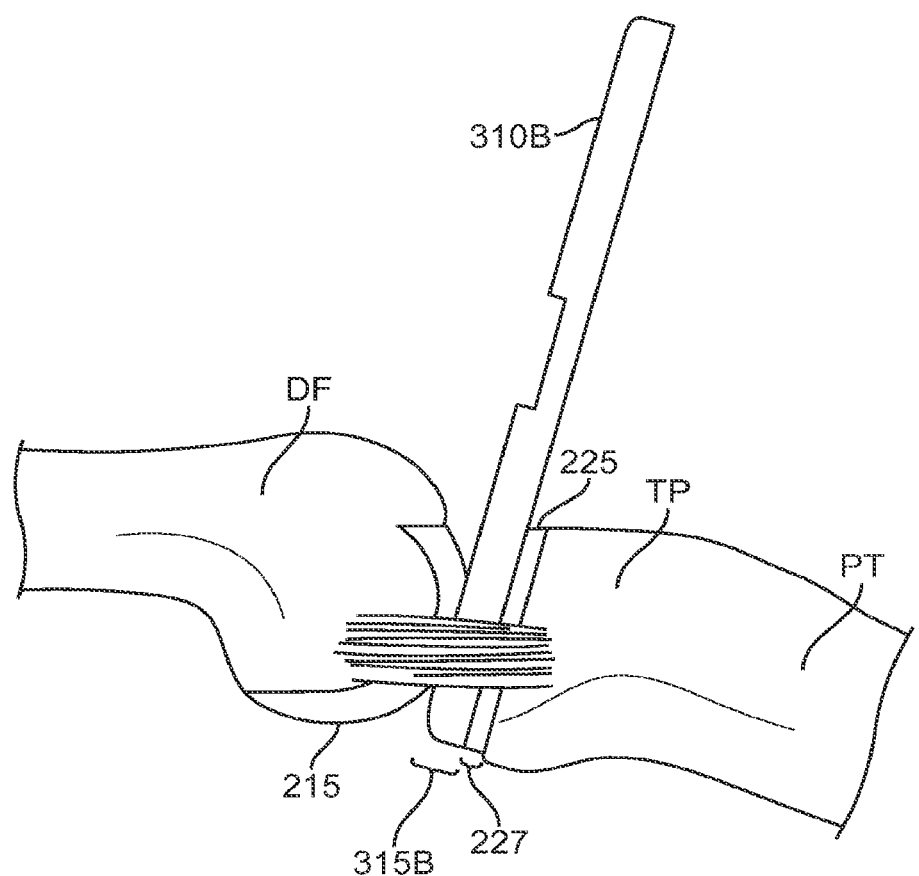

Referring to FIGS. 3A and 3B, a plurality of gauge shims may be used to facilitate the balancing of knee ligament tension during an exemplary UKA procedure. A medial or lateral condyle of a femur and a medial or lateral tibial plateau are cut or milled down. The knee is then placed in 90 degrees of flexion. Femoral member or template prosthesis 215 is inserted and lightly secured to the cut femoral condyle. Femoral member or template prosthesis 215 is sized and shaped similarly to femoral prosthesis 210, shown in FIG. 2A, but is not permanently attached to the distal femur DF. The thickness of femoral template prosthesis 215 matches the thickness of femoral prosthesis 210. The cut tibial plateau is fit with a tibial member or template prosthesis 225. Tibial template prosthesis 225 is often sized and shaped similarly to tibial prosthesis 220, shown in FIG. 2A, but is not permanently attached to the proximal tibia PT. A plurality of gauge shims can be used to measure the gap between the femoral template prosthesis 215 and the tibial prosthesis 225 in both flexion and extension. When the knee is in 90 degrees of flexion, this gap is referred to as the flexion gap. When the knee is in about 20 degrees of flexion to full extension, this gap is referred to as the extension gap. The gauge shim(s) 310A and 310B can sit on top of the force sensor as shown FIGS. 4B-4C or the gauge shim(s) 310C can attach below the force sensor as shown in FIG. 4E. The gauge shim can have flat, spherical, curved, convex or concave surfaces. On at least one end of each gauge shim is a contact area adapted to contact the condylar portion of femoral template prosthesis 215. A concave surface allows for correct rotational alignment about the same medial/lateral centerline 505 of the femoral component 502 shown in FIG. 5B. The spherically concave region also receives the rounded femoral component in a complimentary fit. Each gauge shim may have a specific thickness, for example, one shim may be 1 mm thick, another may be 2 mm thick, another may be 3 mm thick, another may be 4 mm thick, and another may be 5 mm thick. Individual gauge shims are inserted (i.e. tried) into the flexion gap. As shown in FIG. 3A, gauge shim 310A of a specific thickness 315A achieves "natural tension" in the knee ligaments. The thickness of the flexion gap will often be the thickness 315A of the specific gauge shim 310A which achieves "natural tension." Such "natural tension" can be indicated by the specific gauge shim 310A being able to slide in an out easily of the flexion gap but not tilting when inserted into the flexion gap. This "natural tension" is based on the subjective "feel" of the user or surgeon.

Once the flexion gap is measured, the extension gap is measured. Gauge shim 310A is removed and the knee is moved into an extended position, for example, 20 degrees of flexion. Although moving the knee into other degrees of flexion and extension, such as full extension, is possible, 20 degrees of flexion may be preferable because in full extension the posterior capsule of the knee in extension may be tight and its influence may lead to false under-measurement. At this point in the UKA procedure, the extension gap will often be smaller than the flexion gap. The extension gap is measured in a manner similar to how the flexion gap is measured. As shown in FIG. 3B, individual gauge shims are inserted into the flexion gap until a specific gauge shim 310B of a specific thickness 315B achieves "natural tension" in the knee ligaments. The thickness of the extension gap will often be the thickness 315B of the specific gauge shim 310B which achieves "natural tension." Such "natural tension" can be indicated by the specific gauge shim 310B being able to slide in an out easily of the flexion gap but not tilting when inserted into the extension gap. Again, this "natural tension" is based on the subjective "feel" of the user or surgeon. Further cutting or milling down across the end of the femur can balance the flexion and extension gaps. The thickness of the bone to be cut is equal to the difference between the flexion gap and the extension gap. For example, if the extension gap is measured to be 2 mm and the flexion gap is measured to be 5 mm, then the thickness of bone to be further cut or milled down from the distal femur is 3 mm.

Referring now to FIGS. 4A to 4E, handheld force sensor 100 may be used to facilitate balancing knee ligament tension and balance between the flexion gap and extension gap in an exemplary UKA procedure. A medial or lateral femoral condyle, a medial or lateral end of the distal femur, and a medial or lateral tibial plateau are cut or milled down. The knee is then placed in approximately 90 degrees of flexion. Femoral template prosthesis 215 is inserted and lightly secured to the cut femoral condyle. As shown in FIG. 4A, instead of fitting the tibial plateau TP with tibial template prosthesis 225 as in the UKA procedure of FIGS. 3A and 3B, handheld force sensor 100 can be placed in the flexion gap so that thin distal portion 130, shown in FIG. 1A, is placed over and covers the cut or milled down portion of the tibial plateau TP. Thin distal portion 130 may have a surface area matching that of tibial template prosthesis 225, shown in FIG. 3B. The thickness 135 of thin distal portion 130 can substantially match the thickness 227 of tibial template prosthesis 225. Stop portion 140A or 140B may prevent handheld force sensor 100 from being advanced too far into the knee. In the embodiment shown in FIG. 4A, processor 155 of handheld force sensor 100 may be coupled to a visual display 180 through a connection 190. Connection 190 may be a wired connection, for example, a USB connection, a coaxial cable connection, an Ethernet cable connection, or the like, or may be a wireless connection, for example, a BlueTooth® connection, a radiofrequency connection, an infrared connection, Z-Wave connection, Zigbee® connection or other wireless personal area network (WPAN), for example. FIGS. 4A-4E show alternative embodiments of visual display 180 that can be adapted to display usable force and/or pressure data from processor 155 on screen 185. Screen 185 may comprise, for example, an LCD display or an LED display. Visual display 180 can also display force and/or pressure data that may be stored in tangible media coupled to or integrated with processor 155. Such tangible media may comprise, for example, volatile or non-volatile memory, including random access memory (RAM) or flash memory, respectively. Referring to FIG. 4E, the data may be visually displayed 180 via code. The visual display comprises a plurality of different colored lights. Each light is illuminated in response to discrete incremental changes in force applied to the sensor element. Each illuminated light corresponds to an increase of force applied to the sensor. Each light could also be separately illuminated in response to a different predetermined force detected by the sensor element. For example, green light 186A indicates acceptable force, yellow light(s) 186B indicates marginally acceptable force and red light 186 C indicates unacceptable force. The lights could also be illuminated sequentially or in some other manner so as to indicate changes in measured force.

As shown in FIG. 4B, handheld force sensor 100, along with a plurality of gauge shims as described above, can facilitate the measurement of the flexion gap which, in this case, is the gap between thin distal portion 130 and femoral template prosthesis 215 when the knee is in flexion. The gauge shims will often have a flat surface and can be slid over flat top surface 110 of handheld force sensor 100. The lengths of the gauge shims may match the length of handheld force sensor 100. Individual gauge shims are slid over flat top surface 110 of handheld force sensor 100 and placed in the flexion gap until a specific gauge shim 310A of specific thickness 315A achieves "natural tension" in the knee ligaments for the flexion gap. The thickness of the flexion gap will often be the thickness 315A of the specific gauge shim 310A which achieves "natural tension." Such "natural tension" can be indicated by the specific gauge shim 310A being able to slide in an out easily of the flexion gap but not tilting when inserted therein. Handheld force sensor 100 provides a subjective force and/or pressure measurement when this "natural tension" is achieved. The measurement data may be stored and displayed through screen 185.

After the flexion gap is measured, the extension gap, or the gap between thin distal portion 130 and femoral template prosthesis 215 when the knee is extended, is measured. Gauge shim 310A and/or handheld sensor 100 is removed and the knee is placed in an extended position, for example, 20 degrees of flexion. Although moving the knee into other degrees of flexion and extension, such as full extension, is possible, 20 degrees of flexion may be preferable because in full extension the posterior capsule of the knee in extension may be tight and its influence may lead to false undermeasurement. At this point in the UKA procedure, the extension gap is often less than the flexion gap. The extension gap is measured in a manner similar to how the flexion gap is measured. As shown in FIG. 4C, handheld force sensor 100 is placed in the extension gap and individual gauge shims are slid over flat top surface 110 of handheld force sensor 100 and placed in the extension gap until a specific gauge shim 310B of thickness 315B achieves "natural tension" in the knee ligaments for the extension gap. The thickness of the extension gap will often be the thickness 315B of the specific gauge shim 310B which achieves "natural tension." Such "natural tension" can be indicated by the specific gauge shim 310B being able to slide in an out easily of the flexion gap but not tilting when inserted therein. Handheld force sensor 100 provides a subjective force and/or pressure measurement when this "natural tension" is achieved. The measurement data may be stored and displayed through screen 185. Ideally, the "natural tension" achieved for the extension gap should result in the same force and/or pressure measurements as the "natural tension" achieved in the knee ligaments for the flexion gap. As described above, further cutting or milling down across the end of the femur based on the difference between the thickness of the flexion and extension gaps can balance the flexion and extension gaps and knee ligament tension. The thickness of the bone to be cut is equal to the difference between the flexion gap and the extension gap. For example, if the extension gap is measured to be 2 mm and the flexion gap is measured to be 5 mm, then the thickness of bone to be further cut or milled down from the distal femur is 3 mm.

Although specific reference is made towards the use of handheld force sensor 100 for UKA procedures, handheld force sensor 100 may also find use for TKA or other similar procedures performed on the knee and other anatomical joints. For example, such anatomical joints may include an elbow joint, an intervertebral joint, a hip joint, an ankle joint, and a shoulder joint. For example, handheld force sensor 100 may be adapted to be used to measure force between the humerus and the ulna in the elbow or between adjacent vertebrae.

Figure 5A:
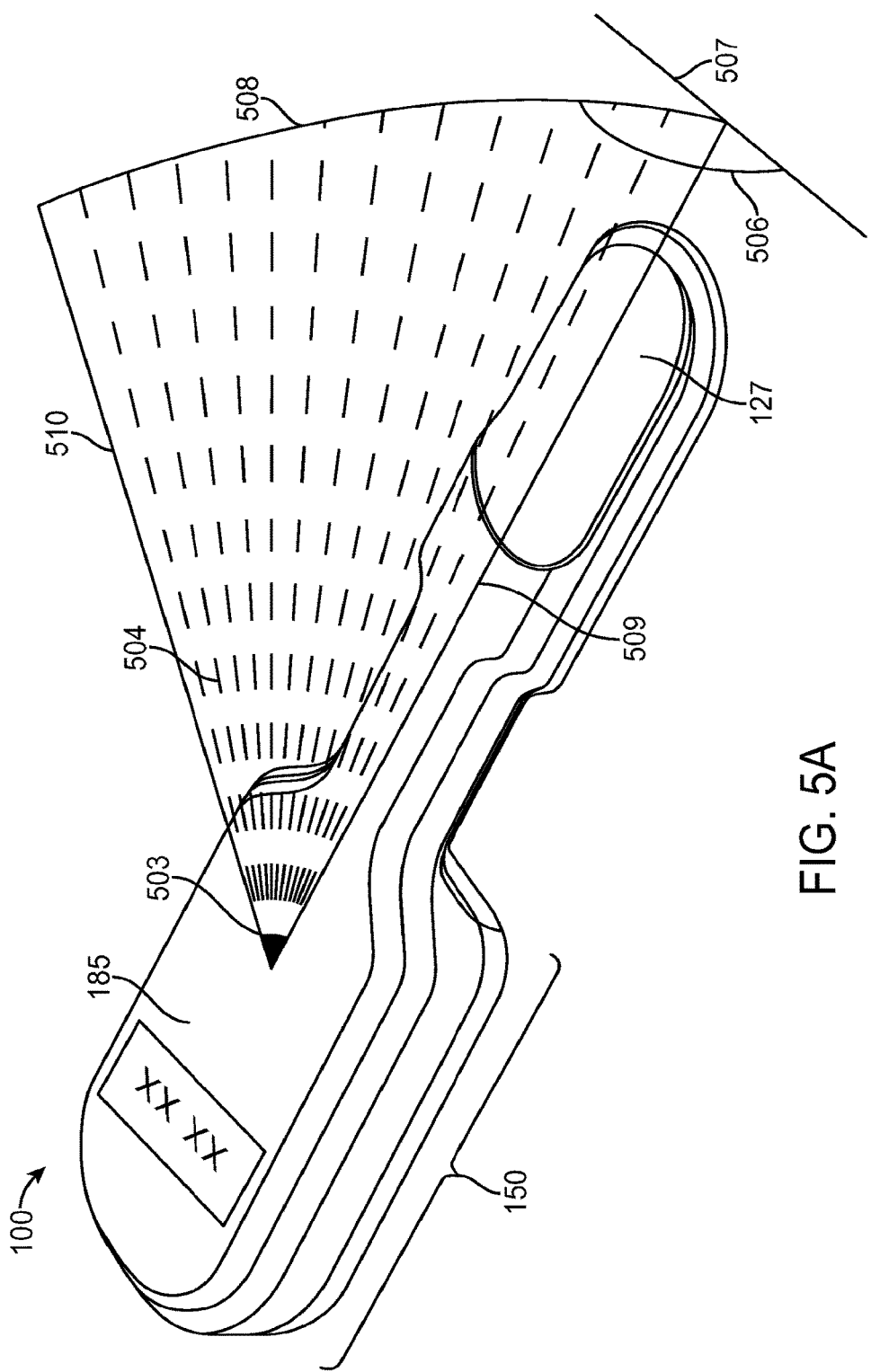
FIG. 5A shows a perspective view of a handheld force sensor with the laser beam activated.
Figure 5B:
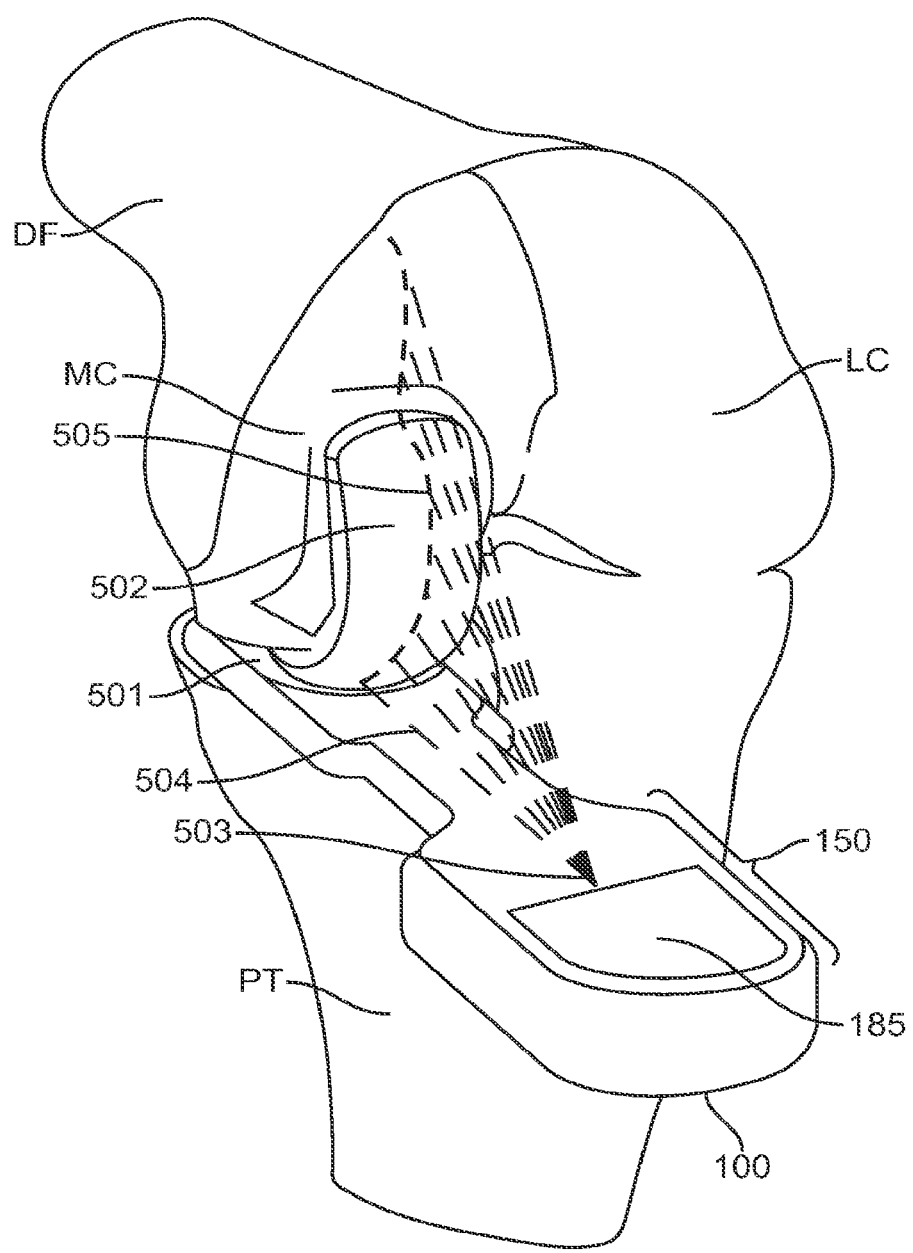
FIG. 5B shows a perspective view of a handheld force sensor deployed in the flexion gap with the laser beam activated.

FIG. 5A shows a perspective view of a handheld force sensor 100 emitting a beam of light 504 from a source 503 on the handle portion 150. The light can be any light visible to the human eye including a laser, for example. The light beam 509 shines toward and across the force sensing pad or member 127 at an upward 90 degree angle 506 creating a height 510 along path 508. The light beam is cast perpendicular to the plane 507 of the force sensing pad 127. The light serves as a visual indication of tilt and alignment to the surgeon when the force sensor 100 is disposed in the flexion gap between a femoral member and a tibial plateau. This is important because the line cast by the light establishes an accurate and repeatable rotational position each time the force sensor is inserted into the gap. The position is established by comparing the alignment of condylar center of the femoral component 505 with the light path 508 during knee arthroplasty. It ensures rotational alignment with the condylar center of the femoral component 505 of the femoral component 502 (i.e. implant). FIG. 5B shows a perspective view of the handheld force sensor deployed in the flexion gap with the laser beam shinning up the face of the femoral component 502.

Figure 5C:
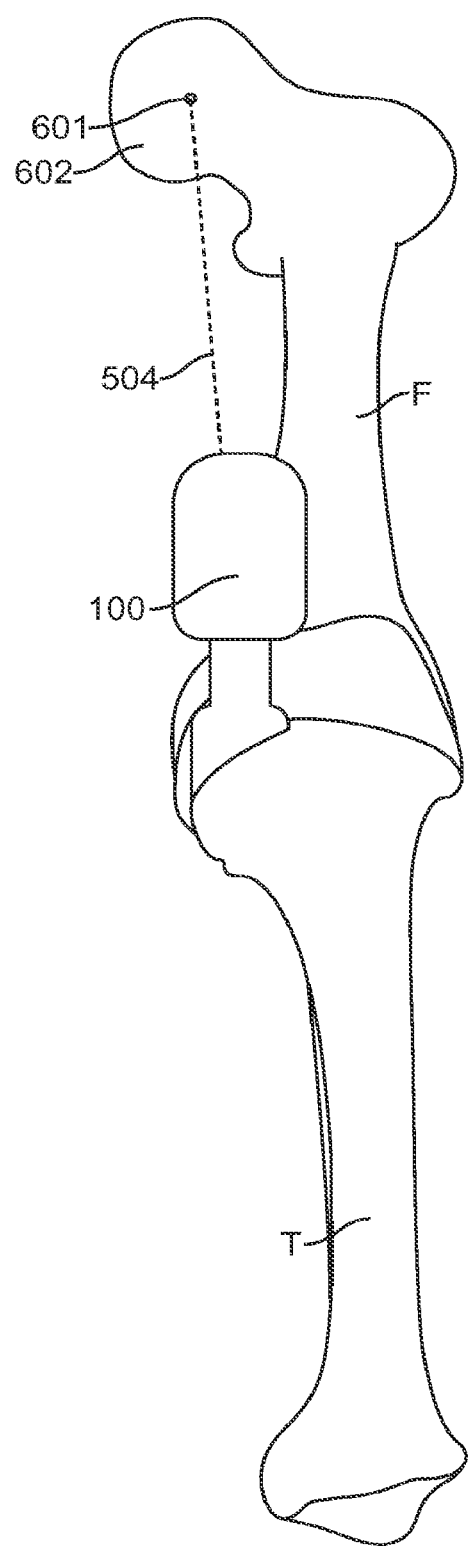
FIG. 5C shows a perspective view of a handheld force sensor deployed in the extension gap with the laser beam activated.

FIG. 5C shows a perspective view of a handheld force sensor deployed in the extension gap with laser beam activated. FIG. 5D depicts a rotated view of FIG. 5C including a perspective view of a handheld force sensor deployed in the extension gap with the laser beam activated. A view of the hip center location 601 is visualized as the beam of light 504 is directed along the femur F. During extension, the beam of light 504 can be directed toward the hip, giving a visual cue to the surgeon as to the location of the hip center location 601 on or about the femoral head 602. This is important because it helps to determine the location of the mechanical or anatomical axis of the leg during knee arthroplasty, for example.

Figure 5E:
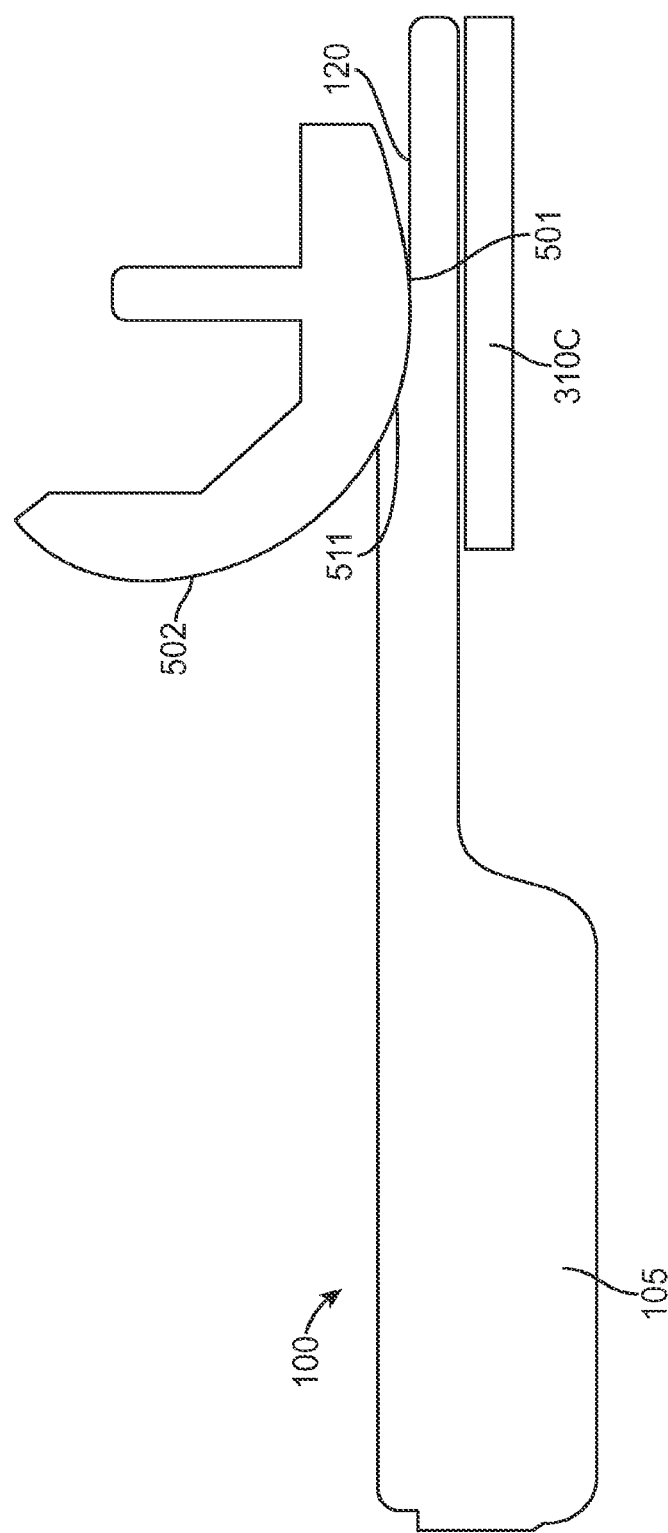
FIG. 5E shows a side view of a surface interface between a handheld force sensor and a condylar surface.

FIG. 5E shows a side view of a surface interface 511 located between a concave force sensing pad 501 and a condylar surface 502. The concave shape avoids edge-loading of the force sensing pad 501 as a result of the contact area climbing up the radial/articular side walls. The concave shape also prevents differing anterior/posterior insertion positions because the condylar surface repeatedly fits into the same position on the force sensing pad 501. Alternatively, the sensing element can have flat, spherical, convex or curved surfaces, for example.

While the above is a complete description of the preferred embodiments of the invention, various alternatives, modifications, and equivalents may be used. Therefore, the above description should not be taken as limiting in scope of the invention which is defined by the appended claims.

What is claimed is:

1. A system for measuring a force or a pressure in a space within one side of an anatomical joint at a time, the system comprising:
   a hand-held unicompartmental sensor configured to measure a force or a pressure generated between one of opposing medial condyles or opposing lateral condyles within the anatomical joint, the unicompartmental sensor configured to measure the force or pressure generated between one set of opposing condyles at a time, the unicompartmental sensor comprising an elongate housing and a sensor element, the elongate housing comprising a thin distal portion, including the sensor element, and a proximal handle portion.

2. The system of claim 1, wherein the anatomical joint is a knee and the force or pressure in the space within one side of the anatomical joint are caused by ligaments adjacent the knee.

3. The system of claim 1, wherein the anatomical joint is selected from the group consisting of an elbow joint, an intervertebral joint, a hip joint, an ankle joint, and a shoulder joint.

4. The system of claim 1, wherein the elongate housing further comprises a stop portion proximal of the thin distal portion and distal of the proximal handle portion, the stop portion including a thickness greater than the thin distal portion to limit an insertion distance of the hand-held unicompartmental sensor into the anatomical joint.

5. The system of claim 4, wherein the stop portion includes a transparent material or an opening to allow light to pass through.

6. The system of claim 4, wherein the stop portion is attached perpendicular to a distal end of the thin portion.

7. The system of claim 1, wherein the sensor element comprises a plurality of force sensing pads or a plurality of force sensing members.

8. The system of claim 1, wherein the sensor element is selected from the group consisting of piezoelectric sensors, force sensing resistors, force sensing capacitors, strain gages, load cells, and pressure sensors.

9. The system of claim 1, wherein the thin distal portion of the elongate housing comprises a wide distal region shaped to conform to a medial compartment or a lateral compartment of the anatomical joint and a thin proximal region, and the force sensing member of the sensor element is disposed within the wide distal region of the elongate housing.

10. The system of claim 9, wherein the anatomical joint is a knee joint, the medial compartment is defined by a medial femoral condyle and the medial tibial plateau and the lateral compartment is defined by a lateral femoral condyle and the lateral tibial plateau.

11. The system of claim 1, further comprising:
a processor, coupled with the sensor element, configured for processing sensed force or pressure data into usable data for providing to a user; and
a visual display, communicatively coupled with the processor, configured to display the usable data.

12. The system of claim 11, wherein the visual display is integrated into the proximal handle portion.

13. The system of claim 11, wherein the visual display comprises a plurality of different colored lights, wherein a light is illuminated in response to discrete incremental changes in force or pressure applied to the sensor element, and wherein each illuminated light corresponds to an increase of force or pressure applied to the sensor.

14. The system of claim 11, wherein the visual display comprises a plurality of different colored lights, and wherein each light is separately illuminated in response to a different predetermined force or pressure detected by the sensor element.

15. The system of claim 11, wherein the visual display is wirelessly coupled with the processor.

16. The system of claim 15, wherein the visual display is wirelessly coupled with the processor through at least one of an infrared connection or a radiofrequency connection.

17. The system of claim 11, further comprising tangible media coupled to at least one of the processor and the visual display, the tangible media configured to store a value of the sensed force or pressure data.

18. The system of claim 1 further comprising a gauge shim, the gauge shim including a concave portion having a condylar contact area.

19. The system of claim 18, wherein a length of the thin distal portion matches a length of the condylar contact area of the gauge shim.

20. The system of claim 18, wherein the elongate housing includes a flat first side and a tapered second side opposite the first side, the tapered bottom surface having a greater thickness toward a proximal end of the elongate housing.

21. The system of claim 20, wherein the flat first side is configured to match a side of the gauge shim.

22. The system of claim 1, wherein the proximal handle portion is thicker than the thin distal portion.

23. The system of claim 1, further comprising:
a light source attached to the proximal handle portion;
a femoral prosthetic component configured to attach to one of a medial or lateral femoral condyle; and
a tibial plateau prosthetic attached to at least one of the medial or lateral tibial plateau,
wherein the anatomical joint is a knee; and
wherein the light source is configured to emit a line of visible light across the thin distal portion toward an anterior portion of a distal femur so as to capture a midline of the condylar center of the femoral prosthetic component when at least a portion of the thin distal portion is disposed in a gap between the femoral prosthetic component and the tibial plateau prosthetic with the knee in flexion.

24. The system of claim 23, wherein the light indicates rotational alignment with the condylar center of the femoral prosthesis component during flexion.

25. The system of claim 23, wherein the light is a laser.

26. The system of claim 1, further comprising;
a light source attached to the proximal handle portion;
a femoral prosthetic member configured to at least temporarily attach to one of a medial or lateral condyle of a femur;
a tibial plateau prosthetic configured to at least temporarily attach to a tibia; and
wherein the anatomical joint is a knee, and
wherein the light source is configured to emit a line of visible light across the thin distal portion toward a hip to capture a location of a hip center when the unicompartmental sensor is at least partially disposed in a gap between the femoral prosthetic member and the tibial plateau with the knee in extension.

27. The system of claim 26, wherein the light is a laser.

28. A handheld device for measuring forces in the space within one side of an anatomical knee joint at a time, the device comprising:
an elongate housing and a sensor element configured to measure forces generated between one of opposing medial condyles or opposing lateral condyles in the anatomical joint, the elongate housing and the sensor element configured to measure the forces generated between one set of opposing condyles at a time, the elongate housing comprising a thin force sensing distal portion, including the sensor element, and a proximal handle portion.

29. The device of claim 28, wherein the elongate housing further comprises a stop portion proximal of the thin force sensing distal portion and distal the proximal handle portion, the stop portion limits insertion distance of the handheld device into the anatomical joint.

30. The device of claim 29, wherein the stop portion is thicker than the thin distal force sensing portion.

31. The device of claim 28, wherein the measured forces within the anatomical knee joint are measured between a medial femoral condyle and a medial tibial plateau or between a lateral femoral condyle and a lateral tibial plateau.

32. The device of claim 28, wherein the sensor element comprises a plurality of force sensing members.

33. The device of claim 32, wherein the plurality of force sensing members are selected from the group consisting of piezoelectric sensors, force sensing resistors, force sensing capacitors, strain gages, load cells and pressure sensors.

34. The device of claim 32, wherein the thin force sensing distal portion of the elongate housing comprises a wide distal region and a thin proximal region, and wherein the wide distal region includes the sensor element.

35. The device of claim 34, wherein the sensor element further comprises a distal wiring portion extending proximally of the force sensing member and through the thin proximal region.

36. The device of claim 28, further comprising:
a processor, coupled with the sensor element, configured for processing sensed force data into usable data for providing to a user; and
a visual display, communicatively coupled with the processor, configured to display the usable data.

37. The device of claim 36, further comprising a power source coupled with the sensor element and the processor.

38. The device of claim 28, further comprising a gauge shim removeably coupled to at least a portion of the elongate housing, and wherein the elongate housing has a flat first side and a tapered second side opposite the first side.

39. The device of claim 38, wherein the gauge shim removeably coupled to the flat first side of the elongate housing.

40. The device of claim 28, wherein the proximal handle portion is thicker than the thin distal portion.

* * * * *